United States Patent
Meng et al.

(10) Patent No.: US 10,780,039 B2
(45) Date of Patent: Sep. 22, 2020

(54) PERSONAL CARE COMPOSITION

(71) Applicant: Conopco, Inc., Englewood Cliffs, NJ (US)

(72) Inventors: Sheng Meng, Shanghai (CN); Andrew Malcolm Murray, Neston (GB); Wenhui Song, Shanghai (CN); Su Yuan, Shanghai (CN); Wei Zhao, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 101 days.

(21) Appl. No.: 16/305,522

(22) PCT Filed: May 9, 2017

(86) PCT No.: PCT/EP2017/061001
§ 371 (c)(1),
(2) Date: Nov. 29, 2018

(87) PCT Pub. No.: WO2017/211525
PCT Pub. Date: Dec. 14, 2017

(65) Prior Publication Data
US 2020/0163865 A1    May 28, 2020

(30) Foreign Application Priority Data

Jun. 10, 2016  (WO) ............... PCT/CN2016/085387
Jul. 18, 2016  (EP) ..................................... 16179937

(51) Int. Cl.
| | |
|---|---|
| A61K 8/891 | (2006.01) |
| C08G 77/00 | (2006.01) |
| A61Q 19/00 | (2006.01) |
| A61K 8/92 | (2006.01) |
| A61K 8/96 | (2006.01) |
| C08G 77/42 | (2006.01) |

(52) U.S. Cl.
CPC ............... *A61K 8/891* (2013.01); *A61K 8/92* (2013.01); *A61K 8/965* (2013.01); *A61Q 19/007* (2013.01); *C08G 77/80* (2013.01); *C08G 77/42* (2013.01)

(58) Field of Classification Search
CPC ................. C08G 77/42; C08G 77/80
See application file for complete search history.

(56) References Cited

U.S. PATENT DOCUMENTS

| | | | |
|---|---|---|---|
| 2005/0244351 A1 | 11/2005 | Reinhart et al. | |
| 2008/0206172 A1* | 8/2008 | Mohammadi | A61K 8/33 424/60 |
| 2013/0045260 A1 | 2/2013 | Yamaguchi | |
| 2013/0056360 A1* | 3/2013 | Lu | C25D 11/026 205/96 |
| 2013/0079368 A1* | 3/2013 | Omura | A61Q 19/007 514/315 |
| 2014/0154294 A1* | 6/2014 | Finjan | A61K 8/895 424/401 |
| 2016/0194455 A1 | 7/2016 | Mateu et al. | |

FOREIGN PATENT DOCUMENTS

| | | |
|---|---|---|
| FR | 2582313 | 11/1986 |
| JP | 2006213679 | 8/2006 |
| WO | WO9818849 | 5/1998 |
| WO | WO2007054492 | 5/2007 |
| WO | WO2013060559 | 5/2013 |
| WO | WO2014170865 | 10/2014 |
| WO | WO2014204937 | 12/2014 |

OTHER PUBLICATIONS

Search Report and Written Opinion in PCTEP2017061001; dated Jul. 3, 2017.
Search Report and Written Opinion EP16179937; dated Oct. 28, 2016.
Search Report and Written Opinion in PCTEP2017062290; dated Sep. 28, 2017; World Intellectual Property Org. (WIPO).
Search Report and Written Opinion in EP16179928; dated Oct. 31, 2016; European Patent Office (EPO).
Co-Pending Application; entitled Personal Care Composition; Filed on Nov. 29, 2018.

* cited by examiner

*Primary Examiner* — Marc S Zimmer
(74) *Attorney, Agent, or Firm* — Ellen Plotkin

(57) ABSTRACT

A personal care composition is disclosed comprising from 1 to 90% by weight of a hydrocarbon oil of an average carbon chain length with 8 or higher carbon atoms; a blend of silicone elastomer and solvent; and a cosmetically acceptable carrier; wherein the solvent is a volatile silicone oil selected from octamethylcyclotetrasiloxane, decamethylcyclopentasiloxane, dodecamethylcyclohexasiloxane, blends of methyl trimethicone and dimethicone and mixtures thereof; and wherein the silicone elastomer has the chemical structure of formula I.

16 Claims, No Drawings

PERSONAL CARE COMPOSITION

TECHNICAL FIELD OF THE INVENTION

The invention concerns a personal care composition, especially a personal care composition comprising silicone elastomer and petrolatum that has improved stability and good sensorial property.

BACKGROUND OF THE INVENTION

Hydrocarbon oils are widely used in personal care products to provide various types of skin care and protection by minimizing friction and/or reducing moisture loss. However, they usually have sensory negatives perceived by consumers. Because of the oil/greasy feel, hydrocarbon oils have certain limits to the scope of application.

Silicone elastomers can be employed to improve the sensorial properties of such compositions. Silicone elastomer, as used herein, means cross-linked particles of a silicone polymer that swells significantly in a solvent forming a space filling material which behaves as a visco-elastic soft solid. Generally, the silicone elastomers are used in a blend of silicone elastomer and solvent, which is a dispersion of the silicone elastomer in the solvent.

Most conventional silicone elastomers are siloxanes containing neither hydrophilic nor hydrophobic part, which leads to poor compatibility with many organic oils including hydrocarbon oils such as mineral oil, wax or petrolatum. It is difficult to obtain stable compositions when high levels of hydrocarbon oils are incorporated into the compositions due to the poor compatibility between the two. The structure of the blend of silicone elastomers and solvent may collapse which render it ineffective in providing desired sensorial properties.

Different approaches were developed to improve the compatibility between silicone elastomers and organic oils, including optimizing solvent/elastomer blends, adding or changing the solvents, and/or adding modified polydimethicone polymer into the silicone elastomers. However, these approaches do not provide satisfactory sensory and are cost ineffective.

It is of increasing interest to develop ways to stabilize compositions comprising hydrocarbon oils that result in excellent sensory benefits.

The present inventors have now found unexpectedly that the compatibility between the silicone elastomers and organic oils can be improved by using functional silicone elastomers, which are silicone elastomers modified by grafting hydrophobic and/or hydrophilic groups onto the backbones of elastomers. The functional silicone elastomers used in this invention are alkyl modified, phenyl modified and/or dual (alkyl and phenyl) modified silicone elastomers. It has been found that the functional silicone elastomers showed improved compatibility with hydrocarbon oils. Particularly, the dual (alkyl and phenyl) modified silicone elastomer shows the best compatibility with hydrocarbon oils, providing a personal care composition with enhanced stability and desired sensorial property.

SUMMARY OF THE INVENTION

In a first aspect, the present invention is concerned with a personal care composition comprising:
(i) from 10 to 90% by weight of a hydrocarbon oil of an average carbon chain length with 8 or higher carbon atoms;
(ii) a blend of silicone elastomer and solvent; and
(iii) a cosmetically acceptable carrier;
wherein the solvent is a volatile silicone oil selected from octamethylcyclotetrasiloxane, decamethylcyclopentasiloxane, dodecamethylcyclohexasiloxane, blends of methyl trimethicone and dimethicone and mixtures thereof; and wherein the silicone elastomer has the chemical structure of formula I, wherein:
each $R_1$ is independently $C_{4-36}$ alkyl chain, preferably $C_{8-18}$;
each $R_2$ is independently phenyl or $CH_3$;
each $R_3$ is independently phenyl; and
each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

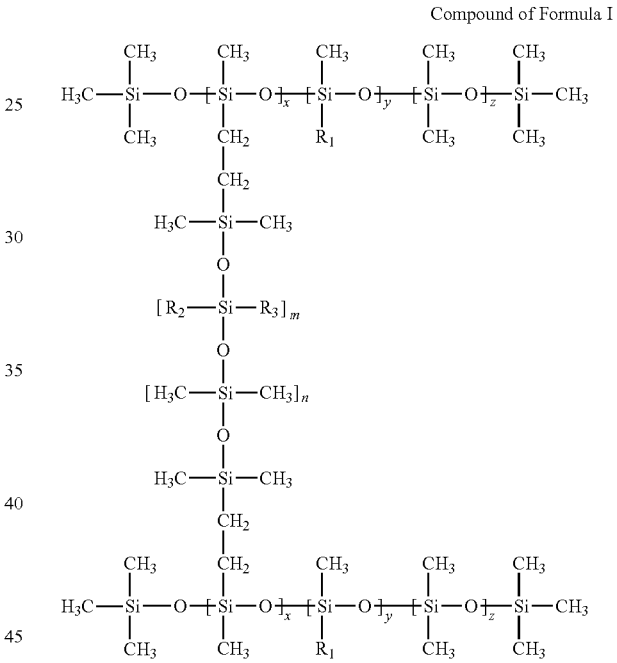

Compound of Formula I

In a second aspect, the present invention is directed to a packaged personal care product comprising the personal care composition of the first aspect of this invention.

In a third aspect, the present invention is directed to a method of using the personal care composition of any embodiment of the first aspect of this invention to provide moisturizing benefit.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word "about".

All amounts are by weight of the final personal care composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION

Now it has been found that functional silicone elastomers which are modified by alkyl, phenyl or dual (alkyl and phenyl) groups showed improved compatibility with hydrocarbon oils. Particularly, the dual (alkyl and phenyl) modified silicone elastomer shows the best compatibility with hydrocarbon oils, providing a personal care composition with enhanced stability and desired sensorial property.

Alkyl mole content as used herein, means the ratio of moles of alkyl substituted dimethicone units to the total moles of dimethicone units per mole of silicone elastomer unit, unless otherwise specified.

Phenyl mole content as used herein, means the ratio of moles of phenyl substituted dimethicone units to the total number of dimethicone units per mole of silicone elastomer unit, unless otherwise specified.

Hydrocarbon Oil

Suitable hydrocarbon oils of the invention include cyclic hydrocarbons, straight chain aliphatic hydrocarbons (saturated or unsaturated), and branched chain aliphatic hydrocarbons (saturated or unsaturated). Hydrocarbon, as used herein, refers to an organic compound consisting entirely of hydrogen and carbon.

The hydrocarbon oil preferably has an average carbon chain length with 8 or higher carbon atoms. Illustrative yet non-limiting examples of the types of hydrocarbon oils that may be used in this invention include, for example, mineral oil, wax, petrolatum and mixtures thereof.

Petrolatum which is known as petroleum jelly is a purified mixture of semi-solid hydrocarbons obtained from petroleum with a carbon chain length with 25 or higher carbon atoms. The petroleum jelly has excellent moisturizing property and has a melting point ranging from a little below to a few degrees above 37° C. It is colorless or pale yellow (when not highly distilled), translucent and devoid of taste and smell when pure. It is insoluble in water. In a preferred embodiment, the hydrocarbon oil comprises or is petrolatum. A commercially available example of a suitable petroleum jelly for use in the invention is MERKUR® 620 from Sasol.

Typically, the personal care composition of the present invention comprises from 1 to 90% by weight of the hydrocarbon oils, more preferably from 3 to 50%, most preferably from 5 to 40%, based on the total weight of the personal care composition and including all ranges subsumed therein.

A Blend of Silicone Elastomer and Solvent

Silicone elastomer, as used herein, means cross-linked particles of a silicone polymer that swells significantly in a solvent forming a space filling material which behaves as a visco-elastic soft solid. Generally, the silicone elastomers are used in a blend of silicone elastomer and solvent, which is a dispersion of the silicone elastomer in the solvent. The blends of silicone elastomer and solvent are cross-linked gels that can be prepared through a hydrosilylation reaction. The reaction involves low levels of catalyst, usually platinum derivatives, and is generally run into an adequate solvent. Silicone-hydride (SiH) containing silicone polymers are reacted with di-vinyl materials to link independent silicone chains.

The solvent suitable for dispersing silicone elastomers is a low molecular weight linear or cyclic silicone oil. The elastomer can be swollen with the low molecular weight silicone oil under a shear force. The low molecular weight silicone oil is preferably a volatile oil, although non-volatile oils can also be used. The volatile silicone oil as per the present invention has a vapor pressure value at 25° C. of 2.6 to 1400 Pa. Particularly preferred volatile oils are linear siloxanes containing from 3 to 9 silicon atoms, and cyclic siloxanes having from 4 to 6 silicon atoms such as cyclopentasiloxane.

In a preferred embodiment, the solvent is a volatile silicone oil. Illustrative yet non-limiting examples of the types of volatile silicone oils that may be used in this invention as a solvent for silicone elastomers include, for example, hexamethylcyclotrisiloxane, octamethylcyclotetrasiloxane, decamethylcyclopentasiloxane, dodecamethylcyclohexasiloxane, blends of methyl trimethicone and dimethicone and mixtures thereof or the like. Examples of commercially available volatile silicone oils include oils having grade designations 344, 345, 244, 245 and 246 from Dow corning Corporation. In a preferred embodiment, the volatile silicone oil is decamethylcyclopentasiloxane, which is made commercially available, for example, from supplier like Dow Corning Corporation under the trade name DC245.

In a preferred embodiment, the blend of silicone elastomer and solvent is a blend of silicone elastomer and volatile silicone oil.

Typically, the blend of silicone elastomer and solvent comprises from 30 to 96% by weight of the solvent, more preferably from 50 to 94%, and most preferably from 67 to 92%.

Silicone elastomers suitable for use in the present invention are functional silicone elastomers that are modified by grafting functional groups onto the backbones of elastomers. In an especially preferred embodiment, the functional silicone elastomers used in this invention are alkyl modified, phenyl modified and/or dual (alkyl and phenyl) modified silicone elastomers.

Alkyl modified functional silicone elastomer may be prepared from the reaction of a) a silicone-hydride containing polysiloxane; b) an alkene; and c) a vinyl-terminated dimethylpolysiloxane by using a hydrosilylation catalyst.

The silicone-hydride containing polysiloxane has the general formula:

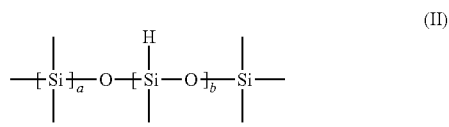

wherein:

each a is independently an integer from 0 to 300, preferably from 5 to 50; and each b is independently an integer from 2 to 300, preferably from 5 to 30.

Silicone-hydride content as used herein, means the moles of silicone-hydride groups per gram of polysiloxane. Typically, the silicone-hydride content of the polysiloxane ranges from 0.016 to 16.6 mM/g, more preferably from 1 to 10 mM/g, and most preferably from 3 to 8 mM/g, based on the total weight of the polysiloxane and including all ranges subsumed therein.

Additionally or alternatively, the silicone-hydride containing polysiloxane has a viscosity from 10 to 1000 centistokes (cSt), preferably from 20 to 500 cSt, more preferably from 25 to 150 cSt, and most preferably from 30 to 80 cSt.

Suitable silicone-hydride containing polysiloxanes which are commercially available include Andisil XL-10, Andisil XL-11, Andisil XL-15 from AB Specialty Silicones.

The alkene is an unsaturated hydrocarbon that contains at least one carbon-carbon double bond. Alkenes have two hydrogen atoms less than the corresponding alkane (with the same number of carbon atoms) with the general formula $C_nH_{2n}$. Preferably, the alkene suitable for use in the reaction has carbon chain lengths ranging from $C_8$ to $C_{18}$. Illustrative yet non-limiting examples of the alkenes that may be used in this reaction include, for example, octene, nonene, decene, undecene, dodecene, tridecene, tetradecene, pentadecene, hexadecene, heptadecene, octadecene, or mixtures thereof. Preferably, the alkene is octene, dodecene, hexadecene or mixtures thereof.

The vinyl-terminated dimethylpolysiloxane has the general formula:

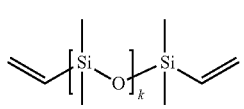

(III)

wherein:
each k is independently an integer from 4 to 1000, preferably from 40 to 500.

The vinyl-terminated dimethylpolysiloxane contains vinyl side groups which may be available for reaction with silicone-hydride containing polysiloxane.

Vinyl content as used herein, means the moles of vinyl group per gram of the vinyl-terminated dimethylpolysiloxane. Typically, the vinyl content of the vinyl-terminated dimethylpolysiloxane ranges from 0.05 to 3 mM/g, more preferably from 0.1 to 1 mM/g, and most preferably from 0.2 to 0.8 mM/g, based on the total weight of the vinyl-terminated dimethylpolysiloxane and including all ranges subsumed therein.

Additionally or alternatively, the vinyl-terminated dimethylpolysiloxane has a viscosity from 10 to 1000 cSt, preferably from 20 to 500 cSt, more preferably from 50 to 400 cSt and most preferably from 100 to 250 cSt.

Suitable vinyl-terminated dimethylsiloxanes which are commercially available include Andisil VS-200 from AB Specialty Silicones.

In the reaction, the alkene reacts with the silicone-hydride containing polysiloxane to form an alkyl modified polysiloxane, which reacts with the vinyl-terminated dimethylpolysiloxane to form the alkyl modified silicone elastomer.

The alkyl mole content of the alkyl modified silicone elastomer is typically in the range from 0.01 to 0.99, more preferably from 0.02 to 0.20.

In a preferred embodiment, the alkyl modified functional silicone elastomer has the general formula:

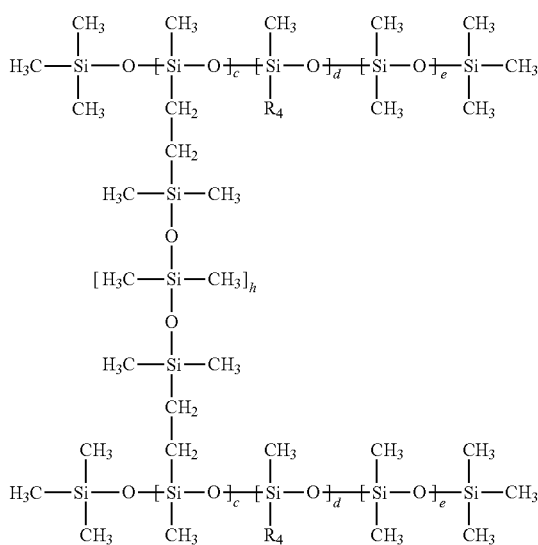

(IV)

wherein:
each $R_4$ is independently $C_{4-36}$ alkyl chain, preferably $C_{8-18}$; and
each c is independently an integer from 3 to 100, preferably from 3 to 20; each d is independently an integer from 1 to 100, preferably from 1 to 20; each e is independently an integer from 1 to 100, preferably from 6 to 50; and each h is independently an integer from 4 to 1000, preferably from 40 to 500.

Phenyl modified functional silicone elastomer may be prepared from the reaction of a) a silicone-hydride containing polysiloxane; and b) a vinyl-terminated dimethyl phenyl polysiloxane by using a hydrosilylation catalyst.

The silicone-hydride containing polysiloxane is the same as described above.

The vinyl-terminated dimethyl phenyl polysiloxane has the general formula:

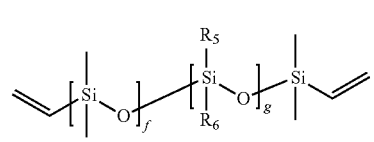

(V)

wherein:
each $R_5$ is independently phenyl or $CH_3$;
each $R_6$ is independently phenyl; and
each f is independently an integer from 4 to 1000, preferably from 40 to 500; and each g is independently an integer from 1 to 100, preferably from 5 to 30.

The vinyl-terminated dimethyl phenyl polysiloxane contains vinyl side groups which may be available for reaction with silicone-hydride containing polysiloxane.

Phenyl mole content as used herein, means the ratio of moles of phenyl substituted dimethicone units to the total moles of dimethicone units of the vinyl-terminated dimethyl phenyl polysiloxane. Typically, the phenyl content of the vinyl-terminated dimethyl phenyl polysiloxane ranges from 1 to 50%, more preferably from 3 to 30% and most preferably from 7 to 15%.

Additionally or alternatively, the vinyl-terminated dimethyl phenyl polysiloxane has a viscosity from 100 to 10000 cSt, preferably from 500 to 8000 cSt, more preferably from 800 to 5000 cSt and most preferably from 1000 to 2000 cSt.

Suitable vinyl-terminated dimethyl phenyl polysiloxane which are commercially available include Andisil SF-2430 from AB Specialty Silicones.

Preferably, the silicone-hydride containing polysiloxane and the vinyl-terminated dimethyl phenyl polysiloxane are present in the reaction mixture in a weight ratio from 1:200 to 200:1, more preferably from 1:50 to 50:1, most preferably from 1:30 to 30:1.

The phenyl mole content of the phenyl modified silicone elastomer is typically in the range from 0.01 to 0.50, more preferably from 0.03 to 0.34.

In a preferred embodiment, the phenyl modified functional silicone elastomer has the general formula:

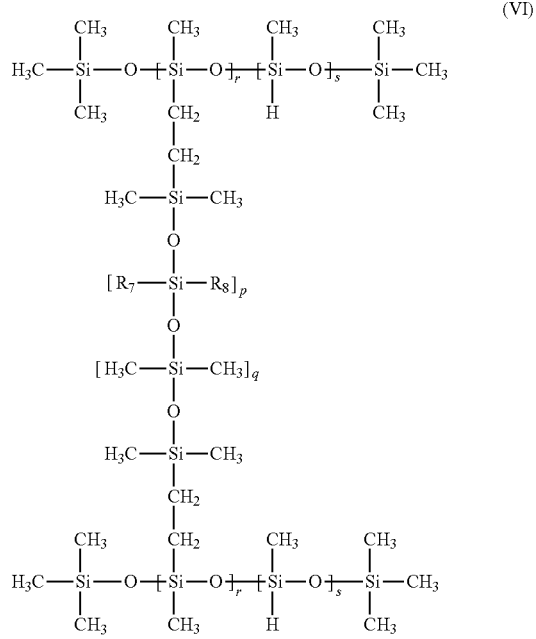

wherein:
each $R_7$ is independently phenyl or $CH_3$;
each $R_8$ is independently phenyl; and
each r is independently an integer from 3 to 100, preferably from 3 to 20; each s is independently an integer from 2 to 200, preferably from 7 to 70; each p is independently an integer from 1 to 100, preferably from 5 to 30; and each q is independently an integer from 4 to 1000, preferably from 40 to 500.

Dual (alkyl and phenyl) modified silicone elastomer may be prepared from the reaction of a) a silicone-hydride containing polysiloxane; b) an alkene; and c) a vinyl-terminated dimethyl phenyl polysiloxane by using a hydrosilylation catalyst.

The silicone-hydride containing polysiloxane, the alkene and the vinyl-terminated dimethyl phenyl polysiloxane are the same as described above.

The dual modified silicone elastomer may be prepared through a two-step synthesis by combining the reactants. In the first step, the alkene reacts with the silicone-hydride containing polysiloxane to form an alkyl modified polysiloxane. In the second step, the left unsubstituted silicone-hydride groups on the alkyl modified polysiloxane react with the vinyl side groups on the vinyl-terminated dimethyl phenyl polysiloxane to form the dual modified silicone elastomer.

For the first step, the temperature of the reaction mixture may be any suitable temperature at which the silicone-hydride containing polysiloxane and the alkene can react to form the alkyl modified polysiloxane. Preferably the temperature of the reaction mixture is from 5° C. to 100° C., more preferably from 10° C. to 80° C. and most preferably from 20° C. to 60° C.

The reaction time for the first step is at least 5 mins, more preferably at least 10 mins, most preferably from 20 to 60 mins.

For the second step, the temperature of the reaction mixture may be any suitable temperature at which the alkyl modified polysiloxane and the vinyl-terminated dimethyl phenyl polysiloxane can react to form the dual modified silicone elastomer. Preferably the temperature of the reaction mixture is from 10° C. to 120° C., more preferably from 20° C. to 100° C. and most preferably from 40° C. to 80° C.

The reaction time for the second step is at least 1 hour, more preferably at least 2 hours, most preferably from 3 hours to 6 hours.

The alkyl mole content of the dual (alkyl and phenyl) modified silicone elastomer is typically in the range from 0.01 to 0.99, more preferably from 0.02 to 0.20.

The phenyl mole content of the dual (alkyl and phenyl) modified silicone elastomer is typically in the range from 0.01 to 0.50, preferably from 0.03 to 0.34.

In a preferred embodiment, the dual (alkyl and phenyl) modified silicone elastomer has the general formula:

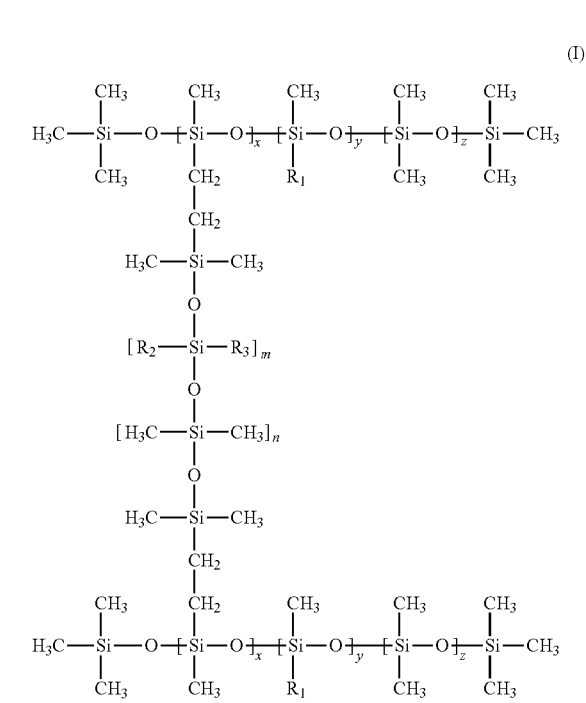

wherein:
each $R_1$ is independently $C_{4-36}$ alkyl chain, preferably $C_{8-18}$;
each $R_2$ is independently phenyl or $CH_3$;
each $R_3$ is independently phenyl; and each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

Typically, the blend of silicone elastomer and solvent comprises from 1 to 70% by weight of silicone elastomer, more preferably from 5 to 50% and most preferably from 8 to 30%.

The blend of silicone elastomer and solvent preferably comprises the silicone elastomer and the solvent in a weight ratio from 1:20 to 2:1, more preferably from 1:15 to 1:1, and most preferably from 1:11 to 1:2.

Typically, the personal care composition of the present invention comprises the blend of silicone elastomer and solvent in an amount of from 0.1 to 95%, more preferably from 10 to 90%, more preferably still from 30 to 85% and most preferably from 40 to 70%, based on the total weight of the personal care composition and including all ranges subsumed therein.

The personal care composition preferably comprises the hydrocarbon oil and the blend of silicone elastomer and solvent in a weight ratio from 1:100 to 2:1, more preferably from 1:50 to 1:1, and most preferably from 1:10 to 1:1.2.

Other Components

The personal care composition of the invention may be in any form including toners, lotions, creams, mousses, serum or gel that is suitable for topical application to the skin. The personal care composition can be either a leave-on or a rinse-off product, preferably a leave-on product, especially a skin care product including skin lotions and skin creams.

The personal care composition of the present invention may further comprise an emollient oil. Suitable emollient oils include, for example, ester of alkoxylated aromatic alcohol with fatty carboxylic acid, esters of polyglycols or diols with fatty carboxylic acid such as caprylic/capric triglyceride, ester of fatty alcohol and fatty acid, alkoxylated derivative of benzyl alcohol and mixtures thereof. Preferably the emollient oil is caprylic/capric triglyceride.

Typically, the personal care composition of the present invention comprises the emollient oil in an amount from 0.01 to 10%, more preferably from 0.1 to 8%, most preferably from 1 to 6%, based on the total weight of the personal care composition and including all ranges subsumed therein.

The personal care composition of the invention comprises a cosmetically acceptable carrier. The carrier may be a liquid or solid material. Typically, carrier is present in an amount ranging from 10 to 99.9%, more preferably from 20 to 95%, most preferably from 40 to 85% by total weight of the personal care composition including all ranges subsumed therein. Suitable carrier classes include water, silicones, polyhydric alcohols, hydrocarbons, triglycerides and thickening powders.

In a preferred embodiment, the personal care composition is anhydrous. Anhydrous, as used herein, refers to a composition comprises less than 1.5% by weight of water, preferably less than 1.0%, and more preferably less than 0.75% and more preferably still less than 0.5%, and even more preferably less than 0.1% and most preferably from 0.0 to 0.01%, based on total weight of the personal care composition, including all ranges subsumed therein.

The personal care composition may further comprise other ingredients which are common in the art to enhance physical properties and performances. Suitable ingredients include but are not limited to, humectants, thickeners, opacifiers, binders, colorants and pigments, pH adjusting agents, preservatives, optics, perfumes, viscosity modifiers, biological additives, buffering agents, conditioners, natural extracts, essential oils and skin benefit agents including anti-inflammatory agents, cooling agents, antiperspirant agents, anti-aging agents, anti-acne agents, anti-microbial agents and antioxidants.

A wide variety of packaging can be employed to store and deliver the personal care compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered as a stick composition formulation in a container with propel-repel mechanism where the stick moves on a platform towards a dispensing orifice. Metallic cans pressurized by a propellant and having a spray nozzle serve as packaging for antiperspirants, shave creams and other sprayable personal care products. Toilet bars may have packaging constituted by a cellulosic or plastic wrapper or within a cardboard box or even encompassed by a shrink wrap plastic film.

The invention is further concerned with a method of using the personal composition to provide moisturizing benefit to the skin of an individual in need thereof.

The following examples are provided to facilitate an understanding of the present invention. The examples are not provided to limit the scope of the claims.

EXAMPLES

Example 1

This example demonstrates the oil compatibility of mixtures of silicone elastomers and white petroleum jelly (WPJ).

Preparation of Blends of Silicone Elastomer and Solvent

Materials

Silicone-hydride containing polysiloxane (Andisil XL-10), vinyl-terminated dimethylpolysiloxane (Andisil VS-200), vinyl-terminated dimethyl diphenyl polysiloxane (Andisil SF-2430) were purchased from AB Specialty Silicones. Decamethylcyclopentasiloxane (DC245) was purchased from Dow Corning Corporation. Platinum catalyst is platinum (0)-1,3-divinyl-1,1,3,3-tetramethyldisiloxane complex solution-in xylene from Sigma Aldrich. White petroleum jelly (MERKUR® 620) was purchased from Sasol. All the chemicals were used as received without further purification.

Solid content, as used herein, refers to the weight percentage of silicone elastomers in the blend of silicone elastomer and solvent.

Non-Functional Silicone Elastomer/DC245 Blend 0.382 g Andisil XL-10, 12 g Andisil VS-200 and 70 g DC245 were mixed in a flask. 25 µL of platinum complex catalyst was added and the reaction mixture was kept at 45° C. with the reflux of water and stirred at 200 rpm for 5 hours. The gelled mixture can be diluted to different solid content at 45° C. after the reaction was completed.

Alkyl Modified Silicone Elastomer/DC245 Blend 1.068 g Andisil XL-10 and 23 g DC245 were mixed and stirred in a vial. 1.1 g isooctene was added into the mixture, followed by the addition of 10 µL platinum complex catalyst. The mixture was stirred at room temperature for 30 mins. Then the reaction mixture was transferred to a flask. 23 g DC245 and 20 g Andisil VS-200 were added into the mixture and then the mixture was kept at 45° C. with the reflux of water and stirred at 200 rpm. 15 µl of platinum complex catalyst was added and the reaction mixture was stirred at 45° C. for 5 hours. The gelled mixture can be diluted to different solid content at 45° C. after the reaction was completed.

Phenyl Modified Silicone Elastomer/DC245 Blend 0.6 g Andisil XL-15, 14 g Andisil SF-2430 and 70 g DC245 were mixed and stirred in a vial, followed by the addition of 25 µL platinum complex catalyst. The mixture was kept at 60° C. with the reflux of water and stirred at 200 rpm for 4 hours. The gelled mixture can be diluted to different solid content at 60° C. after the reaction was completed.

Dual Modified Silicone Elastomer/DC245 Blend 1.02 g Andisil XL-10, 0.94 g dodecene and 4 g DC245 were mixed and stirred in a vial, followed by the addition of 2 µL platinum complex catalyst. The mixture was stirred at 60° C. for 30 mins. Then the reaction mixture was transferred to a flask. 40 g DC245, 20 g Andisil SF-2430 and 6 µL platinum complex catalyst were added to the mixture and the mixture was kept at 60° C. with the reflux of water and stirred at 200 rpm for 4 hours. The gelled mixture can be diluted to different solid content at 60° C. after the reaction was completed.

Methods

The gelled mixtures (blends of silicone elastomer and solvent) were diluted to a solid content of 14.5%. Samples were made by adding WPJ in various gelled mixtures in different amounts ranging from 10% to 40%. The mixtures were stirred well at room temperature, heated at 45° C. for 2 hours and then cooled to the ambient temperature.

Amplitude Sweep Rheology Analysis

In amplitude sweep rheology test, the storage modulus and loss modulus represent the viscoelastic property. Normally, the storage modulus (initial G') represents the elasticity and the loss modulus (initial G") represents the viscosity. Failure points (FP, strain %) with strain percentage represents the stability of the swelling structure of the blend of silicone elastomer and solvent. In general, for in-house silicone elastomers, the acceptable range of the storage modulus (initial G') was from 800 Pa to 4000 Pa in personal care application. For the failure point, above 10% strain means good swelling structure stability.

A physica MCR301 (Anton Paar) Rheometer, which was equipped with 25 mm parallel plates and measure cells, was used for rheological amplitude sweep at 25° C. with 1 mm of measure position and 30 mm of lift position.

The storage modulus profile (G'/Pa) and failure point (FP, strain %) were recorded and summarized in Tables 1 and 2 respectively.

TABLE 1

| Silicone elastomer/DC 245 blend[a] | WPJ[c] wt % in the mixture of WPJ and the blend | | | | |
|---|---|---|---|---|---|
| | 0 | 10 | 20 | 30 | 40 |
| DC9045[b] | 3714 | 3276 | 1285 | 271 | 312 |
| NSE | 1090 | 1139 | 1175 | 630 | 2313 |
| ASE | 1613 | 1805 | 1979 | 1200 | 1389 |

TABLE 1-continued

| Silicone elastomer/DC 245 blend[a] | WPJ[c] wt % in the mixture of WPJ and the blend | | | | |
|---|---|---|---|---|---|
| | 0 | 10 | 20 | 30 | 40 |
| PSE | 1105 | 1176 | 1322 | 1303 | 1651 |
| DSE | 1795 | 2167 | 2344 | 2373 | 2072 |

[a]Silicone elastomer/DC245 blend is selected from in-house prepared non-functional silicone elastomer (NSE)/DC245 blend, alkyl modified silicone elastomer (ASE)/DC245 blend, phenyl modified silicone elastomer (PSE)/DC245 blend and dual modified (alkyl and phenyl) silicone elastomer (DSE)/DC245 blend.
[b]DC9045 is a commercially available non-functional silicone elastomer octamethylcyclotetrasiloxane dispersed in decamethylcyclopentasiloxane from Dow Corning.
[c]White petroleum jelly is commercially available under the trade name MERKUR® 620 from Sasol.

TABLE 2

| Silicone elastomer/DC245 blend[a] | WPJ[c] wt % in the mixture of WPJ and the blend | | | | |
|---|---|---|---|---|---|
| | 0 | 10 | 20 | 30 | 40 |
| DC9045[b] | 60 | 51 | 45 | 25 | 5.5 |
| NSE | 75 | 72 | 52 | 25 | 7.2 |
| ASE | 70 | 70 | 64 | 40 | 13 |
| PSE | 80 | 70 | 64 | 39 | 6.4 |
| DSE | 64 | 64 | 64 | 38 | 20 |

Results

When WPJ was added into the blend of silicone elastomer and solvent in an amount of less than 40 wt %, the structure was dominated by the blend of silicone elastomer and solvent. It can be seen that functional silicone elastomers did give better oil compatibility with WPJ compared to non-functional silicone elastomers.

For the sample comprising DC9045 or in-house prepared non-functional silicone elastomer (NSE), the initial G' and the FP dropped quickly with the increasing of WPJ amount in the mixture, indicating the poor compatibility between the silicone elastomers and WPJ, and the swelling structure of the blend of silicone elastomer and solvent was collapsed. For the sample comprising NSE, the initial G' quickly went up when WPJ was added in an amount of 40 wt %, indicating the structure of the mixture was dominated by WPJ.

For samples comprising functional silicone elastomers, it can be seen that samples comprising ASE or DSE with different amounts of WPJ had both initial G' and FP located in the acceptable range, which indicated the silicone elastomer had good oil compatibility with WPJ and the swelling structure of the blend of silicone elastomer and solvent was well maintained.

Example 2

This example demonstrates the storage stability of compositions comprising silicone elastomers and WPJ. All ingredients are expressed by weight percent by the total formulation, and as level of active ingredient.

TABLE 3

| Ingredient | Percent by weight |
|---|---|
| WPJ[c] | 30 |
| Silicone elastomer/DC245 blend[a] | 57.3 |
| PEG-12 dimethicone | 2 |
| Cerotyl dimethicone | 2 |
| Caprylyl glycol | 0.5 |
| Mica, stearyl triethoxysilane | 1.5 |

TABLE 3-continued

| Ingredient | Percent by weight |
| --- | --- |
| Phenoxyethanol | 0.7 |
| Colloidal oatmeal | 1 |
| Glycerine | 5 |

Methods

In-house prepared blends of silicone elastomer and solvent were prepared as described in Example 1. Samples were made by adding different blends of silicone elastomer and solvent (with a solid content of 14.5%) of the same amount into the base formulation.

Stability Test

Stability, as used herein, refers to the composition maintaining its appearance, odor and main structure without phase separation. When the composition becomes unstable, there is phase separation with some oil leakage observed in the upper layer of the mixtures, which indicates poor storage stability and poor oil compatibility.

Samples were poured into plastic bottles and filled up to ⅔ of the bottles. Then the samples were stored at 50° C. in an oven. For stability test, samples were checked daily. The appearance of samples were observed and recorded. The observation was taken when the samples were still warm and then the samples were left in the oven for 24 hours before another observation was taken. The Samples were stored at 50° C. for 8 weeks, and at the ambient temperature for 8 weeks. The volume of oil leakage was recorded in Table 4.

TABLE 4

| | Volume of Oil Leakage/mL | | | |
| --- | --- | --- | --- | --- |
| Days | NSE | ASE | PSE | DSE |
| 1 | 0 | 0 | 0 | 0 |
| 3 | 1 | 0 | 0 | 0 |
| 5 | 3 | 1 | 0.5 | 0 |
| 8 | 4 | 2 | 1 | 0 |
| 15 | 6 | 4 | 3 | 0 |
| 22 | 7 | 5 | 4 | 0 |
| 44 | 7.5 | 6 | 5 | 2 |
| 51 | 7.5 | 7 | 6 | 2 |
| 57 | 7.5 | 7.5 | 7 | 3 |

Results

It can be seen from the results that samples comprising functional silicone elastomer were much more stable compared to the sample comprising non-functional silicone elastomer, which also indicated the functional silicone elastomer has better oil compatibility with WPJ.

For samples comprising functional silicone elastomers, it further showed that samples comprising DSE gave much better storage stability than samples comprising ASE or PSE.

The invention claimed is:

1. A personal care composition comprising:
   (i) from 1 to 90% by weight of a hydrocarbon oil of an average carbon chain length with 8 or higher carbon atoms;
   (ii) a blend of silicone elastomer and solvent; and
   (iii) a cosmetically acceptable carrier;
   wherein the solvent is a volatile silicone oil selected from octamethylcyclotetrasiloxane, decamethylcyclopentasiloxane, dodecamethylcyclohexasiloxane, blends of methyl trimethicone and dimethicone and mixtures thereof; and wherein the silicone elastomer has the chemical structure of formula I,

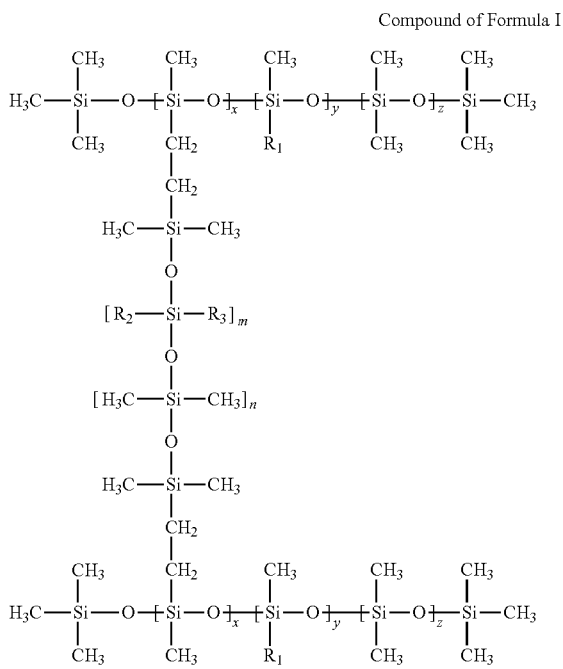

Compound of Formula I wherein:
each $R_1$ is independently $C_{4-36}$ alkyl chain, preferably $C_{8-18}$;
each $R_2$ is independently phenyl or $CH_3$;
each $R_3$ is independently phenyl; and
each x is independently an integer from 3 to 100; each y is independently an integer from 1 to 100; each z is independently an integer from 1 to 100; each m is independently an integer from 1 to 100; and each n is independently an integer from 4 to 1000.

2. The composition as claimed in claim 1 wherein the hydrocarbon oil comprises mineral oil, wax, petrolatum or mixtures thereof, preferably petrolatum.

3. The composition as claimed in claim 2 wherein the petrolatum has a carbon chain length with 25 or higher carbon atoms.

4. The composition as claimed in claim 1 wherein the hydrocarbon oil is present in an amount from 3 to 50%, preferably from 5 to 40% by weight of the composition.

5. The composition as claimed in claim 1 wherein the volatile silicone is decamethylcyclopentasiloxane.

6. The composition as claimed in claim 1 wherein the $R_1$ of the silicone elastomer is a $C_{12}$ alkyl group.

7. The composition as claimed in claim 1 wherein the $R_2$ of the silicone elastomer is a phenyl group.

8. The composition as claimed in claim 1 wherein the alkyl mole content of the silicone elastomer is from 0.01 to 0.99.

9. The composition as claimed in claim 1 wherein the phenyl mole content of the silicone elastomer is from 0.01 to 0.50.

10. The composition as claimed in claim 1 wherein the blend of silicone elastomer and solvent comprises silicone elastomer in an amount of from 1 to 70% by weight of the blend.

11. The composition as claimed in claim 1 wherein the blend of silicone elastomer and solvent comprises the silicone elastomer and the solvent in a weight ratio from 1:20 to 2:1.

12. The composition as claimed in claim 1 wherein the composition comprises the blend of silicone elastomer and solvent in an amount of from 0.1 to 95% by weight of the total composition.

13. The composition as claimed in claim 1 wherein the composition comprises the hydrocarbon oil and the blend of silicone elastomer and solvent in a weight ratio from 1:100 to 2:1.

14. The composition as claimed in claim 1 wherein the composition further comprises an emollient oil.

15. A method for providing moisturizing benefit comprising the step of topically applying the personal care composition as claimed in claim 1 to skin of an individual in need thereof.

16. The composition as in claim 1 wherein:
each x is independently an integer from 3 to 20;
each y is independently an integer from 1 to 20;
each z is independently an integer from 6 to 50;
each m is independently an integer from 5 to 30; and
each n is independently an integer from 40 to 500.

\* \* \* \* \*